(12) United States Patent
Cooke et al.

(10) Patent No.: US 7,575,717 B2
(45) Date of Patent: Aug. 18, 2009

(54) ASSAY DEVICE FOR EVALUATING ENTRAINABLE SUBSTANCES

(75) Inventors: Anthony Cooke, Cambridge (GB); Ramin Pirzad, St. Ives (GB)

(73) Assignee: City Technology Limited, Hampshire (GB)

( * ) Notice: Subject to any disclaimer, the term of this patent is extended or adjusted under 35 U.S.C. 154(b) by 699 days.

(21) Appl. No.: 10/486,934

(22) PCT Filed: Aug. 16, 2002

(86) PCT No.: PCT/GB02/03792

§ 371 (c)(1),
(2), (4) Date: Feb. 12, 2004

(87) PCT Pub. No.: WO03/016871

PCT Pub. Date: Feb. 27, 2003

(65) Prior Publication Data

US 2004/0180451 A1    Sep. 16, 2004

(30) Foreign Application Priority Data

Aug. 17, 2001 (GB) ................................. 0120126.8

(51) Int. Cl.
*G01N 33/00* (2006.01)
(52) U.S. Cl. .............................. 422/56; 422/55; 422/58; 422/68.1; 422/99; 422/102; 422/104
(58) Field of Classification Search .................. 422/55, 422/56, 58, 68.1, 99, 102, 104
See application file for complete search history.

(56) References Cited

U.S. PATENT DOCUMENTS

| 4,300,910 A | 11/1981 | Pannwitz |
| 4,330,297 A | 5/1982 | Leichnitz |
| 5,096,669 A * | 3/1992 | Lauks et al. ........... 204/403.02 |
| 5,312,593 A | 5/1994 | Rabenecker et al. |
| 5,679,535 A | 10/1997 | Joyce et al. |
| 6,660,527 B2 * | 12/2003 | Stroup ........................ 436/165 |

FOREIGN PATENT DOCUMENTS

| EP | 0 450 850 A2 | 10/1991 |
| GB | 2 046 904 A | 11/1980 |
| GB | 2 053 467 A | 2/1981 |
| GB | 2 122 344 A | 1/1984 |
| GB | 2 341 117 A | 3/2000 |
| GB | 2 350 803 A | 12/2000 |
| JP | 060113817 A | 4/1994 |
| WO | WO 86/02160 A1 | 4/1986 |
| WO | WO 00/77516 A1 | 12/2000 |

OTHER PUBLICATIONS

UK Patent Office Search Report of Nov. 14, 2002.

* cited by examiner

*Primary Examiner*—Sam P Siefke
(74) *Attorney, Agent, or Firm*—TraskBritt

(57) ABSTRACT

Diagnostic testing apparatus for evaluating entrainable substances (e.g. for determining allergen activity in house dust), comprising a housing for collection and testing of entrainable substances, the housing having: an inlet; an outlet; a filter disposed between the inlet and the outlet which is configured to capture substances entrained in air flowing from the inlet to the outlet; a reservoir for storing fluid for use in evaluating substances captured on the filter; and means for releasing stored fluid from the reservoir onto the filter.

23 Claims, 3 Drawing Sheets

ASSAY DEVICE FOR EVALUATING ENTRAINABLE SUBSTANCES

TECHNICAL FIELD

The present invention relates to apparatus for evaluating entrained substances, particularly, but not exclusively, particulate material entrainable in an air flow.

BACKGROUND ART

Current diagnostic tests for surface or airborne contaminants usually involve a number of discrete steps each involving specialist equipment. For example, U.S. Pat. No. 5,679,535 describes a method and apparatus used to collect and determine environmental allergens. Dust samples are collected by attaching a device to a vacuum cleaner, and then the collected dust samples are tested separately using an enzyme amino assay for determination of specific allergens. In another example, U.K. patent application GB 2 351 560 shows schematically the use of apparatus for determining dust mite activity in a sample of dust which has been separately collected.

It is an object of the present invention to provide simplified apparatus which makes it easier for diagnostic tests on entrainable substances (e.g. dust) to be carried out.

DISCLOSURE OF THE INVENTION

In accordance with one aspect of the present invention, there is provided diagnostic testing apparatus for evaluating entrainable substances, comprising a housing for collection and testing of entrainable substances, the housing having: an inlet; and outlet; a filter disposed between the inlet and the outlet which is configured to capture substances entrained in air flowing from the inlet to the outlet; and a reservoir for storing fluid for use in evaluating substances captured on the filter, the reservoir being configured to allow stored fluid to be released from the reservoir onto the filter when evaluating substances captured thereon.

The present applicants believe that by integrating sample collection and analysis into a single device, diagnostic testing is greatly simplified to a level where substances may be evaluated quickly and accurately in a domestic environment by relatively unskilled individuals. The outlet may be configured for attachment to a suction device. For example, the outlet may include a mouthpiece or a coupling for engaging a domestic vacuum cleaner appliance.

The reservoir may be located on the inlet side of the filter. The housing may further comprise a chamber for collecting fluid released from the reservoir which has passed through the filter. The housing may be configured to guide released fluid from the reservoir through the filter to the collection chamber. The reservoir may, for example, be used to store a liquid such as a solvent or surface active ingredient to carry compounds of interest in the substances captured on the filter into the collection chamber. This may be beneficial when targeting trace compounds which might otherwise be masked by bulk contaminants also captured by the filter.

The collection chamber may comprise an active ingredient or reactant for reacting with collected fluid. The reactant may be a colorimetric detection reagent which produces a colour change in the presence of a predetermined analyte. The reagent may include, for example, a chromogenic substance bound to a substrate which is only released to provide the colour change in the presence of the predetermined analyte, e.g. a specific protease. Such calorimetric detection reagents are disclosed in WO00/77516, the entire contents of which are incorporated herein by reference.

The collection chamber may include a display for displaying results of substance evaluation. The display may form part of a chemical measuring instrument, or may simply be a window for reviewing the collected fluid, for example, to determine resultant colour if a calorimetric detection reagent is being used.

The collection chamber may further comprise a compartment for storage of a chemical for use in evaluating collected fluid, the compartment being configured to allow a chemical to be released from the compartment when required. The chemical stored may, for example, include a stop which brings to an end any reaction between the collected fluid and the reactant. The stored chemical may be released manually, perhaps after a predetermined time interval.

The reservoir may have a sealed opening which acts as a valve preventing stored fluid from being released onto the filter until substances captured thereon are to be evaluated. The sealed opening may comprise a frangible member which retains fluid in the reservoir until the integrity of the member is compromised. For example, the reservoir may be formed by a so-called blister-pack which includes a membrane which ruptures when compressed. The frangible member may be located to direct stored fluid from the reservoir onto the filter when ruptured. The reservoir may further comprise an actuator which is operable to rupture the frangible member. The actuator may be configured to puncture the frangible member when moved (e.g. manually) from an inoperative position to an operative position.

The housing may be configured to retain fluid released from the reservoir. The inlet or the outlet may comprise a passageway which projects inwardly into the housing. In this way, any tendency for fluid released from the reservoir to flow out of the housing may be reduced. The passageway may further define a tortuous flow path to make it even more difficult for fluid from the reservoir to escape from the housing. The passageway may include a nozzle configured to direct fluid flow from the inlet towards the filter.

In accordance with another aspect of the invention, there is provided diagnostic testing apparatus for evaluating entrainable substances (e.g. for determining allergen activity in house dust), comprising a housing for collection and testing of entrainable substances, the housing having: an inlet, an outlet; a filter disposed between the inlet and the outlet which is configured to capture substances entrained in air flowing from the inlet to the outlet; a reservoir for storing fluid for use in evaluating substances captured on the filter; and means for releasing stored fluid from the reservoir onto the filter.

BRIEF DESCRIPTION OF THE DRAWINGS

An embodiment of the invention will now be described by way of example with reference to the accompanying drawings in which.

MODES OF CARRYING OUT THE INVENTION

Figure 1:
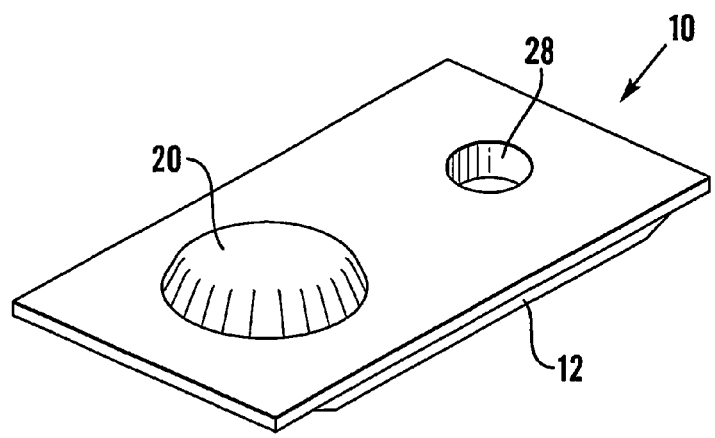
FIG. 1 is a perspective view of diagnostic testing apparatus embodying the present invention.
Figure 2:
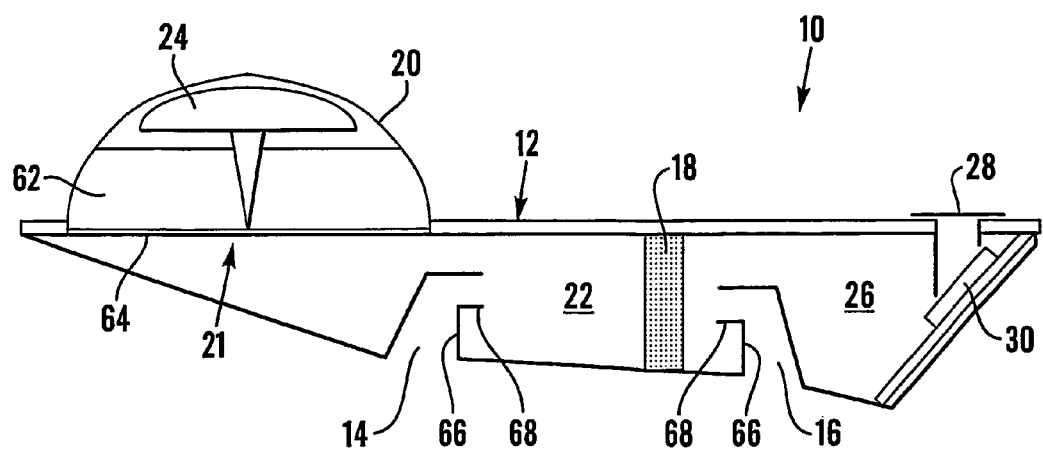
FIG. 2 is a cross-sectional view of the apparatus of FIG. 1.
Figure 3:
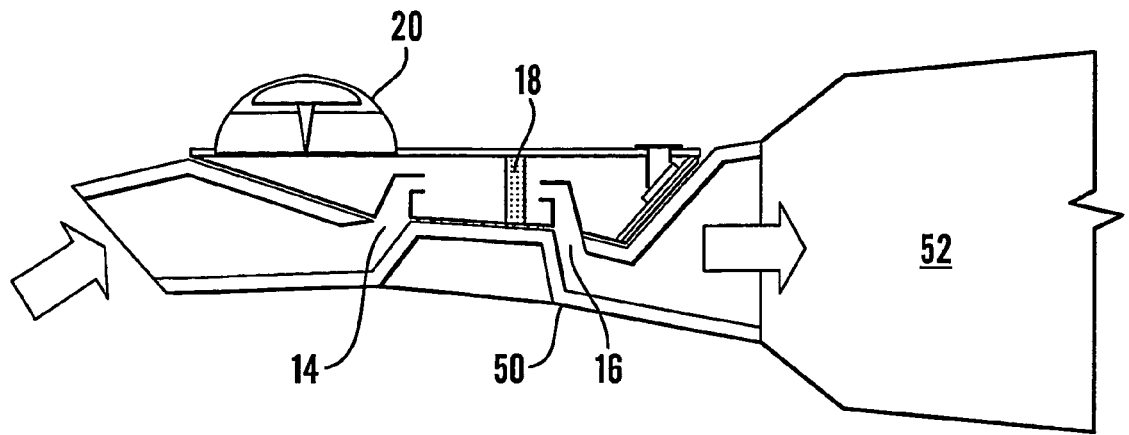
FIG. 3 is a schematic illustration of the apparatus of FIG. 1 in use with a suction device.
Figure 4:
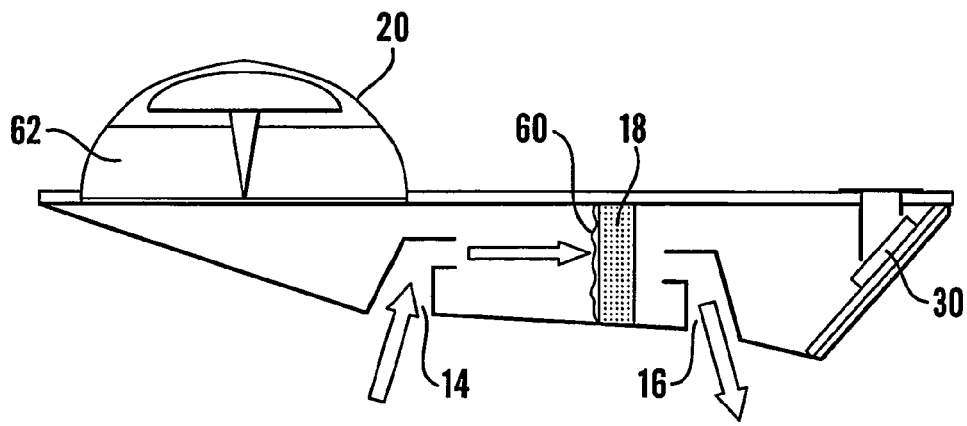
FIG. 4 illustrates schematically airflow through the device of FIG. 1.
Figure 5:
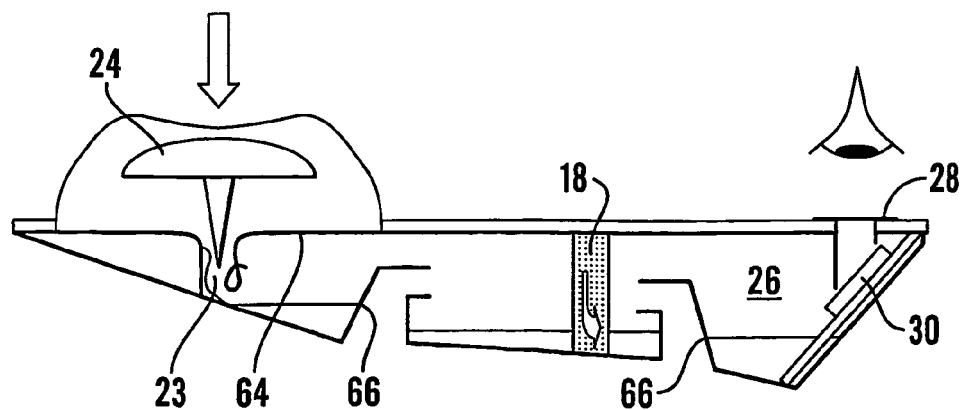
FIG. 5 illustrates schematically release of stored fluid in the device of FIG. 1.

FIGS. 1 and 2 illustrate a disposable diagnostic testing apparatus (10) comprising a housing (12) for collection and evaluation of an entrainable substance. The housing (12) has an inlet (14), an outlet (16), and a filter (18) disposed therebetween. The housing (12) further comprises a sealed reservoir (20) on the inlet side (22) of the filter (18). A manually operated actuator in the form of pin (24) is provided for rupturing reservoir seal (21) to release fluid stored in the reservoir through opening (23) onto the filter (18). The housing (12) further comprises a chamber (26) for collecting fluid passing through the filter (18) and includes a window (28) for viewing the result of a reaction with active ingredients or reactants (30).

The apparatus (10) is secured to a guide (50) which is coupled to a suction device (52) so as to draw air with any contaminants entrained therein through the housing from the inlet (14) towards the outlet (16). The flow of air through the housing (12) causes a residue (60) of substances to build up on the filter (18). The nature of the residue (16) will depend upon the substance being evaluated and the filter (18) will be chosen accordingly.

For example, the filter (18) may comprise fibrous material if particulate matter e.g. house dust or pollen is to be collected, or may comprise activated carbon if organic vapours are to be collected.

The collection of any contaminants is stopped after a predetermined time and the residue (60) is then evaluated. Fluid (e.g. liquid reagent) (62) stored in the reservoir (20) is released into the remainder of the housing (12) by manually depressing a pin (24) to break the reservoir seal (21) by rupturing frangible membrane (64). Fluid released through opening (23) mixes with residue (60) on the filter, and passes through the filter (18) into collection chamber (26). Both the inlet (14) and the outlet (16) include a passageway (66) which projects inwardly into the housing (12) with nozzle (68) spaced from the surrounding walls of the housing. (The passageway (66) does not extend across the full width of the housing (12)). In this way, released fluid flows around the passageway (66) and is prevented from draining out of the housing (12) through the inlet (14) or outlet (16). The fluid may comprise a surfactant or a solvent for extracting the substances of interest and carrying them through the filter (18).

In the collection chamber (26), the reactant or active ingredient (30) is pre-selected to react with the predetermined substance of interest and which has been extracted from the residue (60) by the released fluid. For example, the reactants may be housed in the form of a capillary action lateral flow or flow-through device, or may simply be individual solid or liquid reaction components confined to the collection chamber (26), perhaps in the same way as the stored fluid is retained in reservoir (20) until it is required. For example, a tablet of TNBSA may be provided to react with amino acids or amines extracted from a dust sample (see GB 2 351 560). The progress of any reaction between the collected fluid and the active ingredients (30) may be viewed or measured through the window (28). If colorimetric detection reagents are used, resulting colour will give a visual indication of the level of substances of interest which were present in the residue (60). Otherwise, electronic sensing equipment may be provided with a display to indicate the level of substances of interest which are present in the residue (60).

Figure 6:
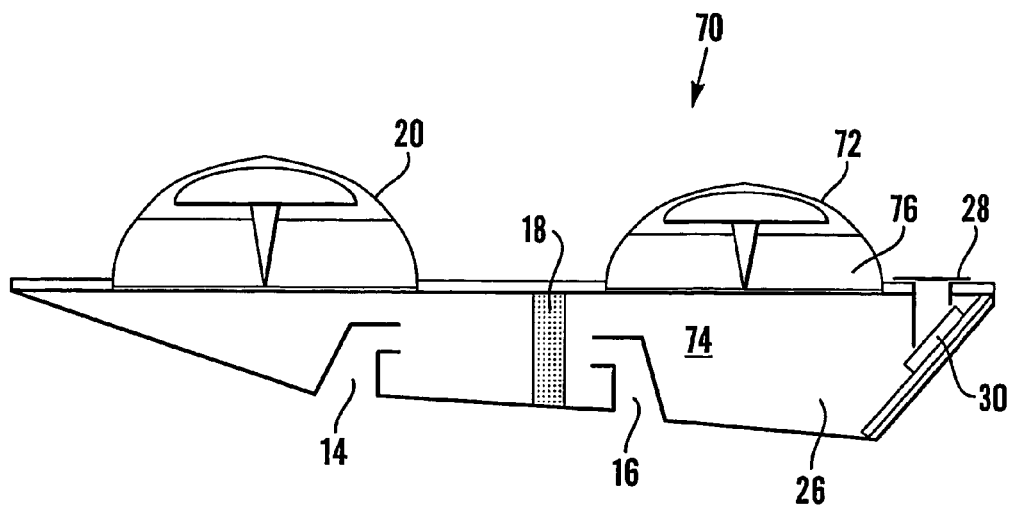
FIG. 6 illustrates a cross-sectional view of a second embodiment of the present invention.

FIG. 6 shows a second embodiment (70) of the present invention (features in common with the embodiment of FIG. 1-5 share the same reference number). The housing (12) includes a sealed compartment (72) on the outlet side (74( ) of filter (18) and which is configured to release compartment contents (76) into the collection chamber (26). The contents (76) may, for example, include a chemical stop to neutralise any reaction between collected fluid and reactants (30) when released from compartment (72) after a predetermined time interval.

Figure 7:
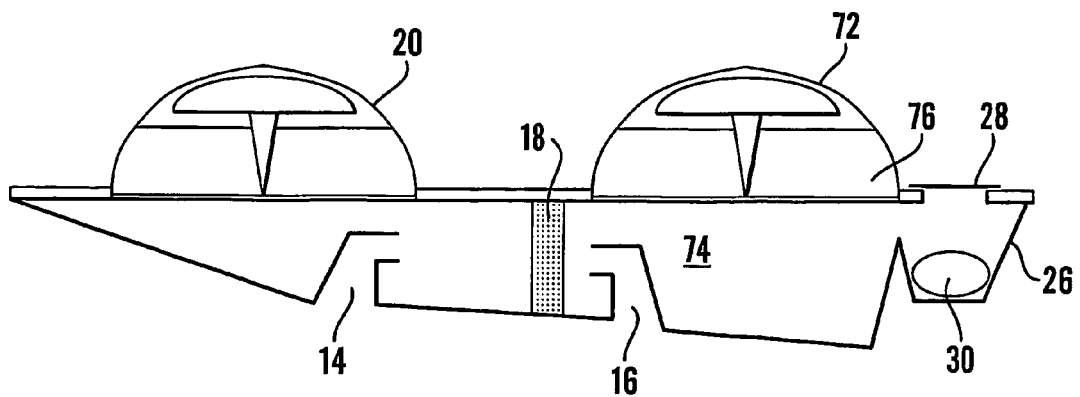
FIG. 7 illustrates a cross-sectional view of a third embodiment of the present invention.

FIG. 7 shows a third embodiment (80) of the present invention (features in common with the embodiments of FIGS. 1-5 and FIG. 6 share the same reference number). An intermediate collection chamber (82) is provided between the filter (18) and the chamber (26) which houses solid reactant (30). A step or weir (84) is provided between the chambers (82) and (26) and is configured to prevent fluid entering the chamber (26) until desired. Thus, for example, intermediate collection chamber (82) enables fluid to be collected from filter (18) and mixed with contents (76) of compartment (72) when released. The resultant mixture may be left to stand for a predetermined time interval before it is allowed to pass over weir (84), e.g. by gently tipping the whole assembly (80).

The invention claimed is:

1. Diagnostic testing apparatus for evaluating dust entrained in an air flow, comprising a housing for collection and testing of entrainable substances, the housing having:
   an inlet;
   an outlet;
   a filter disposed in a flow path defined by the housing between the inlet and the outlet, the filter being configured to capture dust substances entrained in air flowing from the inlet to the outlet; and
   a reservoir located out of the flow path for storing fluid for use in evaluating dust substances captured on the filter, the reservoir being configured to allow stored fluid to be released from the reservoir onto the filter when evaluating dust substances captured thereon; wherein at least one of the inlet and the outlet comprises a passageway which projects inwardly into the housing, defining a nozzle which is spaced from adjacent walls of the housing.

2. Apparatus according to claim 1, in which the reservoir is located on the inlet side of the filter.

3. Apparatus according to claim 2, in which the housing further comprises a chamber for collecting fluid released from the reservoir which has passed through the filter.

4. Apparatus according to claim 3, in which the collection chamber comprises an active ingredient for reacting with collected fluid.

5. Apparatus according to claim 3, in which the collection chamber includes a display for displaying results of substance evaluation.

6. Apparatus according to claim 5, in which the display apparatus comprises a window for viewing contents of the collection chamber.

7. Apparatus according to claim 3, in which the collection chamber further comprises a compartment for storage of a chemical for use in evaluating collected fluid, and means for releasing a chemical stored in the compartment when required.

8. Apparatus according to claim 7, in which the compartment is located out of the flow path.

9. Apparatus according to claim 1, in which the reservoir has an opening with a seal preventing stored fluid from being released through the opening onto the filter until substances captured thereon are to be evaluated.

10. Apparatus according to claim 9, in which the seal comprises a frangible member which prevents stored fluid from being released onto the filter until the member is broken.

11. Apparatus according to claim 10, in which the reservoir further comprises an actuator operable to rupture the frangible member.

12. Apparatus according to claim 1, in which the passageway defines a tortuous flow path, whereby stored fluid released from the reservoir is more readily retained in the housing.

13. Diagnostic testing apparatus for evaluating dust entrained in an air flow, comprising:
  a housing for collection and testing of entrainable substances, the housing having:
    an inlet;
    an outlet;
    a filter disposed in a flow path defined by the housing between the inlet and the outlet, the filter being configured to capture dust substances entrained in air flowing from the inlet to the outlet; and
    a reservoir located out of the flow path for storing fluid for use in evaluating dust substances captured on the filter, the reservoir being configured to allow stored fluid to be released from the reservoir onto the filter when evaluating dust substances captured thereon; and
  a guide defining an air flow path and including:
    a first port through which air flows into the guide;
    a second port coupled to the inlet of the housing and communicating with the first port to enable air to flow into the inlet;
    a third port coupled to the outlet of the housing to enable air to flow out of the outlet; and
    a fourth port for connection to a suction device and communicating with the third port.

14. Apparatus according to claim 13, in which the reservoir is located on the inlet side of the filter.

15. Apparatus according to claim 14, in which the housing further comprises a chamber for collecting fluid released from the reservoir which has passed through the filter.

16. Apparatus according to claim 15, in which the collection chamber comprises an active ingredient for reacting with collected fluid.

17. Apparatus according to claim 15, in which the collection chamber includes a display for displaying results of substance evaluation.

18. Apparatus according to claim 17, in which the display apparatus comprises a window for viewing contents of the collection chamber.

19. Apparatus according to claim 15, in which the collection chamber further comprises a compartment for storage of a chemical for use in evaluating collected fluid, and means for releasing a chemical stored in the compartment when required.

20. Apparatus according to claim 19, in which the compartment is located out of the flow path.

21. Apparatus according to claim 13, in which the reservoir has an opening with a seal preventing stored fluid from being released through the opening onto the filter until substances captured thereon are to be evaluated.

22. Apparatus according to claim 21, in which the seal comprises a frangible member which prevents stored fluid from being released onto the filter until the member is broken.

23. Apparatus according to claim 22, in which the reservoir further comprises an actuator operable to rupture the frangible member.

* * * * *

UNITED STATES PATENT AND TRADEMARK OFFICE
CERTIFICATE OF CORRECTION

PATENT NO. : 7,575,717 B2
APPLICATION NO. : 10/486934
DATED : August 18, 2009
INVENTOR(S) : Cooke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 992 days.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,575,717 B2  Page 1 of 1
APPLICATION NO. : 10/486934
DATED : August 18, 2009
INVENTOR(S) : Anthony Cooke and Ramin Pirzad It is certified that error appears in the above-identified patent and that said Letters Patent is hereby corrected as shown below:

| | | |
|---|---|---|
| COLUMN 1, | LINE 67, | change "calorimetric detection" to --colorimetric detection-- |
| COLUMN 2, | LINE 7, | change "calorimetric detection" to --colorimetric detection-- |
| COLUMN 3, | LINE 62, | change "colorimetrie detection" to --colorimetric detection-- |
| COLUMN 4, | LINES 2-3, | change "FIG. 1-5 share the same reference number)." to --FIGS. 1-5 share the same reference numbers).-- |
| COLUMN 4, | LINES 4-5, | change "on the outlet side (74() of filter (18) and which is configured to release" to --on the outlet side (74) of the filter (18) and is configured to release-- |

Signed and Sealed this

Twenty-third Day of November, 2010

David J. Kappos
*Director of the United States Patent and Trademark Office*